United States Patent [19]

Georgiev et al.

[11] Patent Number: 4,769,471

[45] Date of Patent: Sep. 6, 1988

[54] SUBSTITUTED 3,5-DIPHENYL-3-(1H-1,2,4-TRIAZOL-1-YL-METHYL)-2-METHYLISOXAZOLIDINES

[75] Inventors: Vassil S. Georgiev, Rochester; George B. Mullen, Avon, both of N.Y.

[73] Assignee: Pennwalt Corporation, Philadelphia, Pa.

[21] Appl. No.: 36,838

[22] Filed: Apr. 10, 1987

[51] Int. Cl.$^4$ ................ A01N 43/653; C07D 249/08
[52] U.S. Cl. .................... 548/240; 548/265
[58] Field of Search ........................ 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |

OTHER PUBLICATIONS

Sokolov, S. V. et al., Chemical Abstract, 55:7339, (1961), Abstracting "Isoxazole Compounds III, Synthesis of Some Isoxazolylazoles", Zhur. Obshchei Khim., 30, pp. 1781–1787, (1960).

Kano, H. et al., Chem. Abstract, 62:9139A, (1965), Abstracting French No. 1,376,432, (Oct. 23, 1964).

Kano, H. et al., Chem. Abstract, 63:8367a, (1965), Abstracting French No. 1,380,177, (Nov. 27, 1964).

Takahi, Y. et al., Chem. Abstract, 81:22233c, (1974), Abstracting Japan Kokai No. 7399,336, (Dec. 15, 1973).

Boyce, C. B. et al., Chem. Abstract, 87:23258a, (1977), Abstracting German Offen. No. 2,639,189, (Mar. 10, 1977).

Funaki, Y. et al., Chem. Abstract, 92:128915u, (1980), Abstracting Japan Kokai No. 79, 76,579, (Jun. 19, 1979).

Kelly, R. C. et al., Chem. Abstract, 93:114498u, (1980), Abstracting German Offen. No. 2,918,878, (Nov. 22, 1979).

Haken, P. T. et al., Chem. Abstract, 93:132471j; (1980), Abstracting Brit. Pat. Appln. No. 2,024,218, (Jan. 9, 1980).

*Primary Examiner*—Donald G. Daus
*Assistant Examiner*—Mark W. Noel

[57] ABSTRACT

Substituted 3,5-diphenyl-3-[(1H-1,2,4-triazol-1-yl) methyl]-2-methylisoxazolidines in which hydrogens of their phenyl rings may be replaced by halogen, lower alkoxy, lower alkyl or nitro groups are useful as antifungal agents.

11 Claims, No Drawings

SUBSTITUTED 3,5-DIPHENYL-3-(1H-1,2,4-TRIAZOL-1-YL-METHYL)-2-METHYLISOXAZOLIDINES

BACKGROUND OF THE INVENTION

This invention relates generally to substituted 2-methylisoxazolidines and more specifically to 3,5-diphenyl-3-(1H-1,2,4-triazol-1-ylmethyl)-2-methylisoxazolidine derivatives which are useful as antifungal agents.

BRIEF SUMMARY OF THE INVENTION

In accordance with this invention there are provided compounds of the formula:

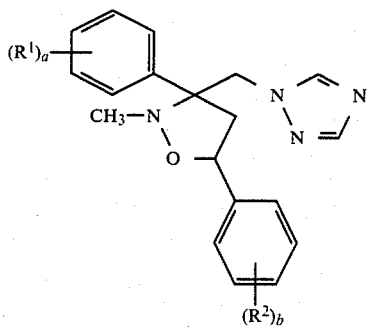

and the pharmaceutically acceptable acid addition salts thereof, in the form of their enantiomers or mixtures of their enantiomers including diastereoisomeric pairs of such enantiomers, wherein;
a=1 or 2,
b=1 or 2,
$R^1$ is selected from hydrogen, lower alkyl, lower alkoxy, halogen, and combinations thereof, provided that the ortho position is hydrogen, and
$R^2$ is selected from hydrogen, lower alkyl, lower alkoxy, halogen, trifluoromethyl, nitro, and combinations thereof.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 1–8, below were found to have good to moderate inhibitory activity against a variety of organisms including epidermophyton floccosum and candida stellatoidea (minimum inhibitory concentration, MIC, of <0.2 to 70 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents and powders in amounts effective to combat systemic and dermatophylic fungal infections in warm blooded animals (1 to 20 percent active ingredient). The compounds of this invention are those of the formula:

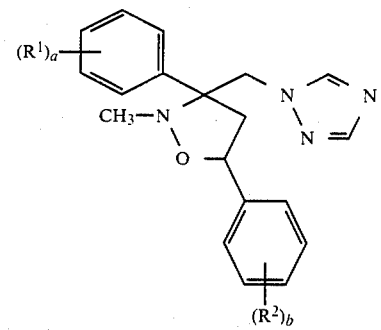

and the pharmaceutically acceptable acid addition salts thereof, in the form of their enantiomers or mixtures of their enantiomers including diastereoisomeric pairs of such enantiomers, wherein;
a=1 or 2,
b=1 or 2,
$R^1$ is selected from hydrogen, lower alkyl, lower alkoxy, halogen, and combinations thereof, provided that the ortho position is hydrogen, and
$R^2$ is selected from hydrogen, lower alkyl, lower alkoxy, halogen, trifluoromethyl, nitro and combinations thereof.

By halogen is meant chlorine, bromine, fluorine and iodine with chlorine and fluorine being preferred. By lower alkyl is meant groups containing one to four (1–4) carbons and by lower alkoxy is meant groups containing one to six (1–6) carbons. In either case such groups having three or more carbons can have a branched or an unbranched chain. Compounds having ortho substitution of the upper phenyl group were not prepared probably due to steric hindrance.

The substituted 3,5-diphenyl-3-(1H-1,2,4-triazol-1-ylmethyl)-2-methylisoxazolidines of the invention are obtained as a mixture of cis- and trans-diastereomers due to the presence to two asymmetric carbon atoms in the isoxazolidine ring. The diastereomeric mixture is conveniently separated by flash-chromatography on silica gel using halogenated hydrocarbons (preferably dichloromethane and chloroform), alkanols (preferably methanol and ethanol), ethyl acetate and such, as eluents. The said eluents may be used alone or in combinations such as the ones comprised of 95–99% by volume halogenated hydrocarbon and 1–5% by volume alkanol. The stereochemistry of the two asymmetric carbon atoms in the isoxazolidine ring may be determined by conventional methods that include x-ray crystallography, nuclear magnetic resonance spectroscopy, circular dichrosim and optical rotatory dispersion. Both the cis and trans stereoisomers are resolvable into their optical enantiomers with (+) and (−) optical rotations by standard techniques such as fractional recrystallization of the diastereometric salts with optically active organic acids such as (+) and (−) -tartaric acid, (+) and (−)-dibenzoyltartaric acid and the like.

The compounds of the invention can be prepared as illustrated in the following diagram. The synthesis of the nitrone precursors 1 is accomplished by reacting an appropriately substituted triazolylacetophenone with N-methylhydroxylamine as described in our copending application Ser. No. 900,856 filed Aug. 27, 1986 whose disclosure is incorporated herein by reference. Subsequent reaction of the properly substituted nitrone precursor 1 with the styrene compound 2 gives the desired 3,5-diphenyl-3-(1H-1,2,4-triazol-1-ylmethyl)-2-methylisoxazolidine analog 3 as a cis-/trans-diastereomeric mixture.

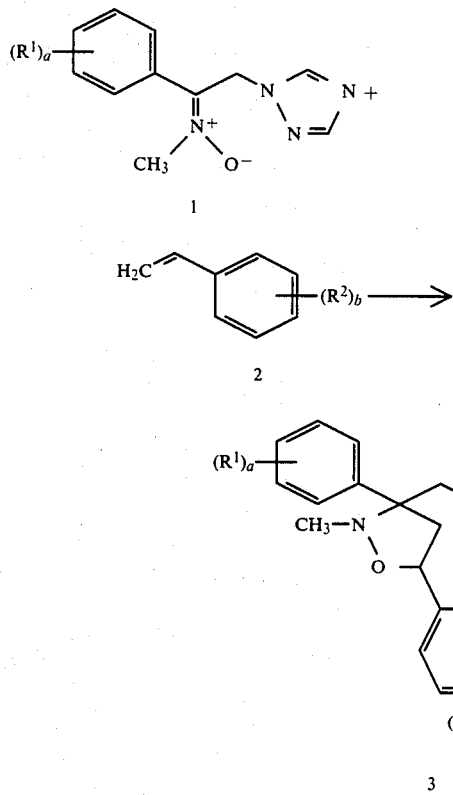

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The styrene derivatives 2 are either commercially available, or may be prepared by standard procedures such as a Wittig reaction of an appropriately substituted benzaldehyde with methylenetriphenylphosphorane [Wittig and Schoellkopf, Chem. Ber. 87, 1318 (1954)]. The preparation of the compounds of the invention is further illustrated by the following examples.

EXAMPLE 1

3-(4-Methoxyphenyl)-5-(3-nitrophenyl)-2-methyl-3-(1H-1,2,4-triazol-1-ylmethyl)isoxazolidine (3: $R^1$=4-OCH$_3$, $R^2$=3-NO$_2$)

A solution of 10.38 g (0.042 mol) of 1-(4-methoxyphenyl)-N-methyl-2-(1H-1,2,4-triazol-1-yl)ethaminine N-oxide (1: $R^1$=4-OCH$_3$) [prepared by reacting 2-(1H-1,2,4-triazol-1-yl)-4'-methoxyacetophenone (32.15 g, 0.148 mol) with N-methylhydroxylamine hydrochloride (19.34 g, 0.232 mol) and NaHCO$_3$ (19.45 g, 0.232 mol) in 300 ml ethanol] and 8.81 ml (0.063 mol) of 3-nitrostyrene (2: $R^2$=3-NO$_2$) in 400 ml toluene is refluxed for 48 hours under a nitrogen atmosphere. Upon cooling to room temperature, the solvent is removed in vacuo, leaving a dark oil containing the cis-/trans- diastereomeric mixture of compound 3 ($R^1$=4-OCH$_3$, $R^2$=3-NO$_2$). Fractional crystallization from ether gave 6.92 g (42%) of isomer A, melting point 147°–150° C. (ethyl acetate). Anal. Calcd. for C$_{20}$H$_{21}$N$_5$O$_4$: C, 60.75; H, 5.35; N, 17.71. Found: C, 60.61; H, 5.35; N, 17.52.

EXAMPLE 2

3,5-Diphenyl-2-methyl-3-(1H-1,2,4-triazol-1-ylmethyl)-isoxazolidine (3: $R^1$=$R^2$=H)

Compound 3 ($R^1$=$R^2$=H) is prepared by a method similar to that described in Example 1 by reacting N-methyl-1-phenyl-2-(1H-1,2,4-triazol-1-yl)ethanimine N-oxide (1: $R^1$=H) with styrene (2:($R^2$=H). The resulting cis-/trans-diastereomeric mixture of compound 3 ($R^1$=$R^2$=H) is purified by fractional crystallization using ethyl acetate. Isomer A has a melting point of 96°–102° C. (ethyl acetate). Anal. Calcd. for C$_{19}$H$_{20}$N$_4$O: C, 71.23; H, 6.29; N, 17.49. Found C, 71.17; H, 6.48; N, 17.41.

EXAMPLE 3

3-Phenyl-5-(4-fluorophenyl)-2-methyl-3-(1H-1,2,4-triazol-1-ylmethyl)isoxazolidine (3: $R^1$=H, $R^2$=4-F)

Compound 3 ($R^1$=H, $R^2$=4-F) is prepared by a method similar to that described in Example 1 by reacting N-methyl-1-phenyl-2-(1H-1,2,4-triazol-1-yl)ethanimine N-oxide (1: $R^1$=H) with 4-fluorostyrene (2: $R^2$=4-F). The resulting cis-/trans-diastereomeric mixture of compound 3 ($R^1$=H, $R^2$=4-F) is flash-chromatographed on neutral silica gel using a 98:2 by volume mixture of chloroform and methanol as eluent. Isomer A has a melting point of 105°–109° C. (ethyl acetate). Anal. Calcd. for C$_{19}$H$_{19}$FN$_4$O: C, 67.44; H, 5.66; N, 16.56; F, 5.61. Found: C, 67.43; H, 5.48; N, 16.64; F, 5.57.

EXAMPLE 4

3-Phenyl-5-(4-methylphenyl)-2-methyl-3-(1H-1,2,4-triazol-1-ylmethyl)isoxazolidine (3: $R^1$=H, $R^2$=4-CH$_3$)

Compound 3 ($R^1$=H, $R^2$=4-CH$_3$) is prepared by a method similar to that described in Example 1 by reacting N-methyl-1-phenyl-2-(1H-1,2,4-triazol-1-yl)ethanimine N-oxide (1: $R^1$=H) with 4-methylstyrene (2: $R^2$=4-CH$_3$). The resulting cis-/trans-diastereomeric mixture of compound 3 ($R^1$=H, $R^2$=4-CH$_3$) is flash-chromatographed on neutral silica gel using 98:2 by volume mixture of chloroform and methanol as eluent. Isomer A has a melting point of 110°–114° C. (ethyl acetate). Anal. Calcd. for C$_{20}$H$_{22}$N$_4$O: C, 71.83; H, 6.63; N, 16.75. Found: C, 71.64; H, 6.66; N, 16.67.

EXAMPLE 5

3-(4-Chlorophenyl)-5-phenyl-2-methyl-3-(1H-1,2,4-triazol-1-ylmethyl)isoxazolidine (3: $R^1$=4-Cl, $R^2$=H)

Compound 3 ($R^1$=4-Cl, $R^2$=H) is prepared by a method similar to that described in Example 1 by reacting 1-(4-chlorophenyl)-N-methyl-2-(1H-1,2,4-triazol-1-yl)-ethanimine N-oxide (1: $R^1$=4-Cl) with styrene (2: $R^2$=H). The resulting cis-/trans-diastereomeric mixture of compound 3 ($R^1$=4-Cl, $R^2$=H) is flash-chromatographed on neutral silica gel using a 99:1 by volume mixture of chloroform and ethanol as eluent. Isomer A has a melting point of 128°–131° C. (ethyl acetate-hexane, 1:1 by volume). Anal. Calcd. for C$_{19}$H$_{19}$ClN$_4$O: C, 64.31; H, 5.40; N, 15.79; Cl, 9.99. Found: C, 64.28; H, 5.42; N, 15.78; Cl, 10.11.

Isomer B has a melting point of 119°–112° C. (ethyl acetate-hexane, 1:1 by volume). Anal. Calcd. for $C_{19}H_{19}ClN_4O$: C, 64.31; H, 5.40; N, 15.79; Cl, 9.99. Found: C, 64.24; H, 5.49; N, 15.78; Cl, 10.08.

EXAMPLE 6

3,5-Bis(4-chlorophenyl)-2-methyl-3-(1H-1,2,4-triazol-1-ylmethyl)isoxazolidine (3: $R^1=R^2=$4-Cl)

Compound 3 ($R^1=R^2=$4-Cl) is prepared by a method similar to that described in Example 1 by reacting 1-(4-chlorophenyl)-N-methyl-2-(1H-1,2,4-triazol-1-yl) ethanimine N-oxide (1: $R^1=$4-Cl) with 4-chlorostyrene (2: $R^2=$4-Cl). The resulting cis-/trans-diastereomeric mixture of compound 3 ($R^1=R^2=$4-Cl) is flash-chromatographed on neutral silica gel using a 98:2 by volume mixture of chloroform and methanol as eluent.

Isomer A has a melting point of 117°–120° C. (ethyl acetate-hexane, 1:1 by volume). Anal. Calcd. for $C_{19}H_{18}Cl_2N_4O$: C, 58.62; H, 4.66; N, 14.39; Cl, 18.21. Found: C, 58.65; H, 4.82; N, 14.21; Cl, 17.85.

EXAMPLE 7

3-(4-Chlorophenyl)-5-(4-fluorophenyl)-2-methyl-3-(1H-1,2,4-triazol-1-ylmethyl)isoxazolidine (3: $R^1=$4-Cl, $R^2=$4-F)

Compound 3 ($R^1=$4-Cl, $R^2=$4-F) is prepared by a method similar to that described in Example 1 by reacting 1-(4-chlorophenyl)-N-methyl-2-(1H-1,2,4-triazol-1-yl) ethanimine N-oxide (1: $R^1=$4-Cl) with 4-fluorostyrene (2: $R^2=$4-F). The resulting cis-/trans-diastereomeric mixture of compound 3 ($R^1=$4-Cl, $R^2=$4-F) is flash-chromatographed on neutral silica gel using a 98:2 by volume mixture of chloroform and methanol as eluent.

Isomer A has a melting point of 138°–140° C. (ethyl acetate-hexane 1:1 by volume). Anal. Calcd. for $C_{19}H_{18}ClFN_4O$: C, 61.21; H, 4.87; N, 15.03; Cl, 9.51; F, 5.10. Found: C, 61.22; H, 4.78; N, 14.95; Cl, 9.63; F, 5.00.

EXAMPLE 8

3-(4-Fluorophenyl)-5-phenyl-2-methyl-3-(1H-1,2,4-triazol-1-ylmethyl)isoxazolidine (3: $R^1=$4-F, $R^2=$H)

Compound 3 ($R^1=$4-F, $R^2=$H) is prepared by a method similar to that described in Example 1 by reacting 1-(4-fluorophenyl)-N-methyl-2-(1H-1,2,4-triazol-1-yl)ethanimine N-oxide (1: $R^1=$4-F) with styrene (2: $R^2=$H). The resulting cis/-trans-diastereomeric mixture of compound 3 ($R^1=$4-F, $R^2=$H) is flash-chromatographed on neutral silica gel using a 98:2 by volume mixture of chloroform and methanol as eluent.

Isomer A has a melting point of 122°–125° C. (ethyl acetate). Anal. Calcd. for $C_{19}H_{19}FN_4O$: C, 67.44; H, 5.66; N, 16.56; F, 5.61. Found: C, 67.07; H, 5.59; N, 16.66; F, 5.55.

EXAMPLE 9

3,5-Bis(4-fluorophenyl)-2-methyl-3-(1H-1,2,4-triazol-1-ylmethyl)isoxazolidine (3: $R^1=R^2=$4-F)

Compound 3 ($R^1=R^2=$4-F) is prepared by a method similar to that described in Example 1 by reacting 1-(4-fluorophenyl)-N-methyl-2-(1H-1,2,4-triazol-1-yl)-ethanimine N-oxide (1: $R^1=$4-F) with 4-fluorostyrene (2: $R^2=$4-F). The resulting cis-/trans-diastereomeric mixture of compound 3 ($R^1=R^2=$4-F) is flash-chromatographed on neutral silica gel using a 98:2 by volume mixture of chloroform and methanol as eluent.

Isomer A has a melting point of 98°–103° C. (ethyl acetate-hexane, 1:1). Anal. Calcd. for $C_{19}H_{18}F_2N_4O$: C, 64.04; H, 5.09; N, 15.72; F, 10.66. Found: C, 63.93; H, 5.05, N, 15.68; F, 10.59.

EXAMPLE 10

3-(4-Methoxyphenyl)-5-(3,4-dimethoxyphenyl)-2-methyl-3-(1H-1,2,4-triazol-1-ylmethyl)isoxazolidine [3: $R^1=$4-OCH$_3$, $R^2=$3,4-(OCH$_3$)$_2$]

Compound 3 [$R^1=$4-OCH$_3$, $R^2=$3,4-(OCH$_3$)$_2$] is prepared by a method similar to that described in Example 1 by reacting 1-(4-methoxyphenyl)-N-methyl-2-(1H-1,2,4-triazol-1-yl)-ethanimine N-oxide (1: $R^1=$4-OCH$_3$) with 3,4-dimethoxystyrene [2: $R^2=$3,4-(OCH$_3$)$_2$]. The resulting cis-/-trans-diastereomeric mixture of compound 3 ($R^1=$4-OCH$_3$), is purified by fractional crystallization using ethyl acetate.

Isomer A has a melting point of 177°–179° C. (ethyl acetate). Anal. Calcd. for $C_{22}H_{26}N_4O_4$: C, 64.38; H, 6.38; N, 13.65. Found: C, 64.01; H, 6.51; N, 13.60.

The compounds of the invention where $R^1$ includes alkyl or combinations of alkyl, alkoxy or halogen can be prepared according to the method of Example 1 by substituting for 2-(1H-1,2,4-triazol-1-y1)-4′-methoxy acetophenone the substituted triazolyl phenylacetophenones, prepared from 4′-methylacetophenone, mp 22°–24° C.,
3′,4′-dichloroacetophenone, mp 72°–74° C.,
4′-chloro-3′-methylacetophenone, bp 254° C., and
3′-methylacetophenone, bp 220° C.

The compound of the invention where $R^2$ includes trifluoromethyl can be prepared according to the method of Example 1 by substituting for 3-nitrostyrene, 3-(trifluoromethyl)styrene, bp 55° C./17 mm.

Salts of the compounds of the invention can be prepared as known in the art, for example, by dissolving the compound in a 10:1 by volume mixture of ethanol and aqueous acid such as HCl or HNO$_3$, evaporating the solvent, and then recrystallizing the crude salt, for example, from methanolether, 1:3 by volume in the case of HCl salts, and ethanol in the case of HNO$_3$ salts.

We claim:

1. A compound of the formula:

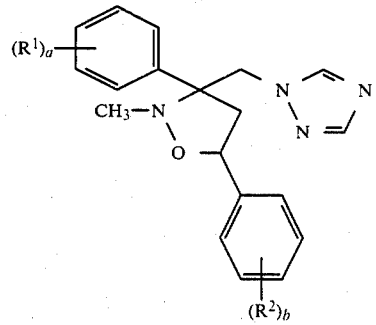

and the pharmaceutically acceptable acid addition salts thereof, in the form of their enantiomers or mixtures of their enantiomers including diastereoisomeric pairs of such enantiomers, wherein;
a=1 or 2,
b=1 or 2, $R^1$ is selected from hydrogen, lower alkyl, lower alkoxy, halogen, and combinations thereof, provided that the ortho position is hydrogen, and $R^2$ is selected from hydrogen, lower alkyl, lower alkoxy, halogen, trifluoromethyl, nitro and combinations thereof.

2. The compound of claim 1 wherein the compound is 3-(4-methoxyphenyl)-5-(3-nitrophenyl)-2-methyl-3-(1H-1,2,4-triazol-1-ylmethyl)isoxazolidine.

3. The compound of claim 1 wherein the compound is 3,5-diphenyl-2-methyl-3-(1H-1,2,4-triazol-1-ylmethyl)-isoxazolidine.

4. The compound of claim 1 wherein the compound is 3-phenyl-5-(4-fluorophenyl)-2-methyl-3-(1H-1,2,4-triazol-1-ylmethyl)isoxazolidine.

5. The compound of claim 1 wherein the compound is 3-phenyl-5-(4-methylphenyl)-2-methyl-3-(1H-1,2,4-triazol-1-ylmethyl)isoxazolidine.

6. The compound of claim 1 wherein the compound is 3-(4-chlorophenyl)-5-phenyl-2-methyl-3-(1H-1,2,4-triazol-1-ylmethyl)isoxazolidine.

7. The compound of claim 1 wherein the compound is 3,5-bis(4-chlorphenyl)-2-methyl-3-(1H-1,2,4-triazol-1-ylmethyl)isoxazolidine.

8. The compound of claim 1 wherein the compound is 3-(4-chlorophenyl)-5-(4-fluorophenyl)-2-methyl-3-(1H-1,2,4-triazol-1-ylmethyl)isoxazolidine.

9. The compound of claim 1 wherein the compound is 3-(4-fluorophenyl)-5-phenyl-2-methyl-3-(1H-1,2,4-triazol-1-ylmethyl)isoxazolidine.

10. The compound of claim 1 wherein the compound is 3,5-bis(4-fluorophenyl)-2-methyl-3-[(1H-1,2,4-triazol-1-ylmethyl)isoxazolidine.

11. The compound of claim 1 wherein the compound is 3-(4-methoxyphenyl)-5-(3,4-dimethoxyphenyl)-2-methyl-3-(1H-1,2,4-triazol-1-ylmethyl)isoxazolidine.

* * * * *